United States Patent [19]

Harada

[11] 4,322,401

[45] Mar. 30, 1982

[54] PERMANENT-WAVE SOLUTION

[76] Inventor: Morio Harada, 4-19 Kamigakicho, Nishinomiya-shi, Hyoga-ken, Japan

[21] Appl. No.: 218,010

[22] Filed: Dec. 18, 1980

[30] Foreign Application Priority Data

Dec. 29, 1979 [JP]  Japan ................................ 54-173538

[51] Int. Cl.$^3$ ............................................... A61K 7/09
[52] U.S. Cl. ..................................................... 424/72
[58] Field of Search .................................... 424/71, 72

[56] References Cited

U.S. PATENT DOCUMENTS

| | | | |
|---|---|---|---|
| 3,242,052 | 3/1966 | Sheffner | 424/71 |
| 3,976,781 | 8/1976 | Kalopissis | 424/71 |
| 4,139,610 | 2/1979 | Miyazaki et al. | 424/71 |

*Primary Examiner*—Donald B. Moyer
*Attorney, Agent, or Firm*—Haight, Rosfeld & Noble

[57] ABSTRACT

Permanent-wave solution comprising an aqueous alkaline solution of cysteine and an organic acid anhydride as added thereto in a molar ratio of 0.1 to 0.5 per each mole of cysteine is disclosed. The solution is stable upon exposure to air while retaining a sufficient curling effect on the hair.

3 Claims, No Drawings

PERMANENT-WAVE SOLUTION

This invention relates to a permanent-wave solution comprising cysteine and an organic acid anhydride such as succinic anhydride, acetic anhydride, etc. (hereinafter referred to sometimes briefly as acid anhydride).

The conventional permanent-wave solution is based on thioglycolic acid but this acid has a fairly harsh action on the hair and is known to cause split hair, loss of hair, discoloration of hair, etc. Moreover, the acid could be a cause of an irritated scalp, various skin disorders, injured hair roots and other adverse effects. Recently, permanent-wave solutions based on cysteine have been developed and employed. While cysteine exerts only a mild action on the hair compared to thioglycolic acid and is therefore a safe agent for application to the hair, solutions containing cysteine have the problem of instability of cysteine itself. Especially when such a permanent-wave solution is applied onto the hair, the cysteine is oxidized as the solution is exposed to the atmosphere so that water-insoluble cysteine crystals separate out. White deposits of cysteine crystals on the hair or on the hands of the beautician were found to be nuisances, for they not only detract from the quality of practice but could cause the beautician to suffer from a skin disorder.

In attempts to overcome the above problems, there have been developed a stabilization method involving the use of thioglycolic acid and ethylenediamine tetraacetate or nitrilotriacetic acid or aqueous solutions thereof (Japanese Patent Publication 14934/1973) and a stabilization method using L-cysteine and D-cysteine in a ratio of 7 to 3 or 3 to 7 so as to prevent precipitation of crystals (Japanese Patent Publication 48504/1974). Further, for the purpose of mitigating the severity of crystallization, it has been proposed to add an N-acylamino acid or a salt thereof to a cysteine-based first permanent-wave solution (Japanese Patent Unexamined Publication 125637/1977) or to add N-acetylcysteine to a cysteine-based permanent-wave solution (Japanese Patent Unexamined Publication 128241/1977).

In the latter method (JPUP 128241/1977), 3% or less of N-acetylcysteine is added to a cysteine-based permanent-wave solution to prevent precipitation of white crystals. It is presumed that the formation of cysteine is thereby inhibited or suppressed or that the oxidation product is converted to a derivative of N-acetylcysteine and, thus, solubilized.

This invention does not involve addition of such a special chemical but provides a stable permanent-wave solution which can be made available by a simple procedure and at low cost.

This invention, therefore, relates to a permanent-wave solution comprising cysteine and an acid anhydride as added in a molar ratio of about 0.1 through about 0.5 to each mole of cysteine under alkaline conditions.

When the acid anhydride is added to an aqueous solution of cysteine under alkaline conditions, there is formed an N-derivative of cysteine according to the following formula:

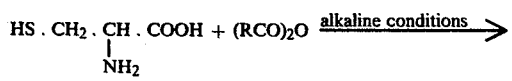

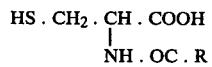

The formation of the above derivative helps to stabilize the solution of cysteine. Moreover, the N-derivative of cysteine which may be produced on atmospheric oxidation is soluble in water or permanent-wave solutions and, therefore, apparently does not separate out as white crystals.

While the type of acid anhydride is not very much critical, it is desirably selected from among acetic anhydride, propionic anhydride, butyric anhydride, succinic anhydride and phthalic anhydride.

In any case, the optimum level of addition of acid anhydride is 0.1 to 0.5 mole to each mole of cysteine. If the molar ratio is less than 0.1, white crystals are still observed, while the use of acid anhydride in excess of 0.5 reduces the amount of active cysteine and, therefore, the solution does not provide a sufficient curling effect on the hair.

The amount of cysteine to be contained in a typical permanent-wave composition is usually about 3 to 15 weight percent. In accordance with this invention, the pH of such a permanent-wave composition is made alkaline so that the acid anhydride may work effectively. Preferably, the composition is adjusted to pH 8 to 10.

The following example is further illustrative of this invention.

EXAMPLE

In 70 ml of pure water was dissolved L-cysteine followed by addition of 0.05 g of tetrasodium EDTA. The mixture was adjusted to pH 9.5 with monoethanolamine, and under stirring a varying amount of acid anhydride was added gradually and evenly dissolved. The solution was adjusted to a final pH of 9.2 with monoethanolamine and diluted with pure water to make a total of 100 ml. The solutions prepared in the above manner were tested.

The results for various acid anhydrides and levels of addition are shown in Tables 1 and 2.

In the control runs without addition of any acid anhydride, the samples were adjusted to pH 9.2 in one operation.

TABLE 1

| Sample No. | L-cysteine (%) | Acetic anhydride (g) | Succinic anhydride (g) | Acid anhydride/ cysteine molar ratio | Crystals on fingers *2 | Crystals in flask *3 |
|---|---|---|---|---|---|---|
| No. 1 | 6.0 | — | — | — | x | 3 |
| No. 2 | " | 0.5 | — | 0.085 | x | 5 |
| No. 3 | " | 1.0 | — | 0.171 | o | 8 |
| No. 4 | " | 2.0 | — | 0.342 | o | 10 |
| No. 5 | " | 3.0 | — | 0.513 | o | 10 |
| No. 6 | " | — | 0.4 | 0.081 | x | 4 |
| No. 7 | " | — | 0.5 | 0.101 | o | 7 |
| No. 8 | " | — | 1.0 | 0.202 | o | 10 |
| No. 9 | " | — | 2.0 | 0.404 | o | 10 |
| No. 10 | " | — | 2.5 | 0.505 | o | 10 |
| No. 11 | " | — | 3.0 | 0.605 | o | 10 |
| No. 12 | 10.0 | — | 0.0 | — | x | 1 |
| No. 13 | " | — | 0.5 | 0.061 | x | 4 |
| No. 14 | " | — | 1.0 | 0.121 | o | 8 |
| No. 15 | " | — | 2.0 | 0.242 | o | 10 |
| No. 16 | " | — | 3.0 | 0.363 | o | 10 |
| No. 17 | " | — | 4.0 | 0.484 | o | 10 |
| No. 18 | " | — | 5.0 | 0.605 | o | 10 |

TABLE 1-continued

| Sample No. | L-cysteine (%) | Acetic anhydride (g) | Succinic anhydride (g) | Acid anhydride/ cysteine molar ratio | Crystals on fingers *2 | Crystals in flask *3 |
| --- | --- | --- | --- | --- | --- | --- |
| No. 19*1 | 4.0 | — | 0.0 | — | x | 4 |
| No. 20 | 4.4 | — | 0.5 | 0.137 | o | 8 |
| No. 21 | 5.0 | — | 1.0 | 0.242 | o | 10 |
| No. 22 | 5.5 | — | 1.5 | 0.330 | o | 10 |
| No. 23 | 6.0 | — | 2.0 | 0.404 | o | 10 |

TABLE 2

| Sample No. | L-cysteine (%) | Succinic anhydride (g) | Phthalic anhydride (g) | Butyric anhydride (g) | Acid anhydride/ cysteine, molar ratio | Crystals on fingers *2 | Crystals in flask *3 |
| --- | --- | --- | --- | --- | --- | --- | --- |
| No. 24 | 5.0 | — | — | | — | x | 3 |
| No. 25 | 5.4 | 0.3 | | | 0.067 | x | 4 |
| No. 26 | 5.6 | 0.5 | | | 0.108 | o | 7 |
| No. 27 | 6.2 | 1.0 | | | 0.195 | o | 9 |
| No. 28 | 7.4 | 2.0 | | | 0.327 | o | 10 |
| No. 29 | 5.4 | | 0.5 | | 0.075 | x | 4 |
| No. 30 | 5.6 | | 0.75 | | 0.109 | o | 7 |
| No. 31 | 6.2 | | 1.5 | | 0.198 | o | 8 |
| No. 32 | 7.4 | | 3.0 | | 0.332 | o | 10 |
| No. 33 | 5.4 | | | 0.6 | 0.085 | x | 5 |
| No. 34 | 5.6 | | | 0.8 | 0.144 | o | 7 |
| No. 35 | 6.2 | | | 1.6 | 0.206 | o | 8 |
| No. 36 | 7.4 | | | 3.2 | 0.345 | o | 10 |

*1 A part of the cysteine incorporated in each formulation reacts with the acid anhydride to give the N-derivative. Therefore, the residual amount of active cysteine in the formulation was determined. The results were 3.95 to 4.10% for Sample Nos. 12 and 20; and 4.9 to 5.1% for Sample Nos. 24 to 36.

*2 Crystals on fingers Each sample was applied in portions of 0.5 ml to 2 interdigital positions for each hand or a total of 4 positions per person, 4 times at 9 and 11 o'clock, a.m. and at 13 and 15 o'clock, p.m. The sample solution was allowed to dry in situ each time and the testers were instructed to wash their hands with soap and water at noon and at 17 o'clock. Using 10 testers, the above procedure was repeated for a week, and their fingers were examined for changes at the sites to which the samples had been applied. Even during the above period, the experiment was immediately discontinued when any sample showed a severe crystallization which might cause a rough skin (marked x in the table). Even if crystalline deposits were found in a few persons on the 4th or 5th day, the experiment was continued unless there was no tendency toward increased precipitation or no further change (marked o in the table).

*3 Crystals in flask A 5 ml portion of each sample was taken in a 500 ml conical flask to prepare a thin liquid layer about 10 cm in diameter on the bottom. The flask was stoppered, allowed to stand in the room and examined for the course of crystallization. The figures in the table represent the days on which crystals began to appear; e.g. "10" means that the sample did not show crystals on 10 days' standing. The sample containing cysteine alone showed crystals all over the surface on the 10th day.

Then, based on the crystallization tendencies shown in Tables 1 and 2, cold permanent-wave tests were performed for all the samples except Nos. 1, 2, 6, 12, 13, 19, 24, 25, 29 and 33.

Each sample was applied to the hair by the conventional method and a cold permanent-wave was applied. The progress of curling practice and the condition of the hair after the treatment were investigated.

(I) During the treatment, none of the samples yielded white crystals.

(II) As to the waves obtained and the sheen of the hair, Sample Nos. 5, 11 and 18 were comparatively weak in the intensity of waves but all other samples produced satisfactory results.

What is claimed is:

1. A permanent-wave solution consisting essentially of an aqueous alkaline solution of a permanent wave effective amount of cysteine and a stabilizing amount of an organic acid anhydride selected from the group consisting of succinic anhydride and phthalic anhydride as solubilizing agent in a molar ratio of about 0.1 to about 0.5 per each mole of cysteine.

2. The permanent-wave solution according to claim 1 wherein said cysteine is contained in a proportion of about 3 to about 15% based on the weight of the permanent-wave solution.

3. The permanent-wave solution according to claim 2 wherein the pH of said permanent-wave solution is between about 8 to about 10.

* * * * *